United States Patent [19]

Toyama et al.

[11] Patent Number: 4,849,279
[45] Date of Patent: Jul. 18, 1989

[54] INSECT-REPELLENT ASSEMBLY

[75] Inventors: Takashi Toyama; Haruyoshi Narita, both of Tokyo; Tatsuya Ishii, Kanagawa, all of Japan

[73] Assignees: Nissho & Co., Ltd.; Toho Rayon Co., Ltd.; Nissan Shoji Co., Ltd., all of Tokyo, Japan

[21] Appl. No.: 159,535

[22] Filed: Feb. 12, 1988

[51] Int. Cl.$^4$ .............................................. D03D 3/00
[52] U.S. Cl. ..................................... 428/224; 428/225; 428/280; 428/284; 428/297; 428/408; 428/905
[58] Field of Search ............... 428/280, 224, 225, 297, 428/408, 905, 284

[56] References Cited

U.S. PATENT DOCUMENTS

| | | | |
|---|---|---|---|
| 4,217,386 | 8/1980 | Arono et al. | 428/408 |
| 4,500,581 | 2/1985 | Mitomi et al. | 428/408 |
| 4,565,727 | 1/1986 | Giglia et al. | 428/408 |
| 4,714,649 | 12/1987 | Edwards | 428/408 |

Primary Examiner—James J. Bell
Attorney, Agent, or Firm—Wegner & Bretschneider

[57] ABSTRACT

An insect-repellent assembly comprising a carrier member containing activated carbon fibers and an insect-repellent agent contained in said carrier member. Cockroach-repellent agents are preferable as the insect-repellent agent. The insect-repellent assembly of the present invention maintains its insect-repellent effect for a extended period of time.

24 Claims, 1 Drawing Sheet

INSECT-REPELLENT ASSEMBLY

BACKGROUND OF THE INVENTION

1. Field of the Invention

The present invention relates to an insect-repellent assembly for preventing insects such as cockroaches from invading the interior of electonic, electric or communication equipment or food storehouses. More specifically, the present invention pertains to an insect-repellent assembly which functions effectively for a long period of time.

2. Description of Prior Art

Recently, air conditioning equipment has come into wide use in houses, restraurants, offices and many other places. Unfortunately this creates improved conditions for insect breeding. As a result, there has been an increase in the number of insects in such places. As the increase in the number of cockroaches has been particularly large, there is now a high probability of cockroaches getting into electronic equipment and the like. If cockroaches invade the interior of such equipment and die there, the skeletons of the cockroaches may cause malfunction of the equipment. To avoid this problem, it has been proposed to apply a cockroach-repellent adjacent to ventilating holes and other places through which cockroaches can enter the equipment. The repellents are usually coated or sprayed on the surfaces or around the holes of the equipment. The repellent agents applied in this way volatilize, vaporize or diffuse and therefore lose their repellent function in a short time. The repellent agent can also be used as coated or sprayed on ordinary paper, webs, formed material or sintered material, but this mode of use cannot be expected to prolong the repellent function for a long time, either.

SUMMARY OF THE INVENTION

It is therefore an object of the present invention to provide an insect-repellent assembly which maintains its repellent effect for a long time.

Another object of the present invention is to provide an insect-repellent assembly which is suitable for use in repelling insects from communication equipment, storehouses and the like.

Still another object of the present invention is to provide a cockroach-repellent assembly which maintains its repellent effect for a prolonged time.

To accomplish the above objects, an insect-repellent assembly according to the present invention comprises a carrier member containing activated carbon fibers, and an insect-repellent agent contained in said carrier member.

The activated carbon fibers can be obtained by activating synthetic fibers such as acrylic fibers, regenerated fibers such as rayon fibers, vegetable fibers such as cotton fibers and animal fibers such as wool fibers. In view of the boiling point and molecular weight of cockroach-repellent agents, the activated carbon fibers preferably have an average specific surface area of about 600–1500 $m^2/g$ and an average diameter of fine pores therein of about 20–30 A. Such activated carbon fibers exhibit a distribution of fine pores suitable for retaining cockroach-repellents which is superior to that of activated carbon particles. In addition, the mass of the above-mentioned activated carbon fibers may have a felt-like, woven-like or random-web-like structure, so that it can easily be shaped into a desired form for an insect-repellent assembly. On the contrary, activated carbon particles are not so easy to form into a shape desirable for an insect-repellent assembly.

The carrier member can be made of activated carbon fibers, while it can also be made by mixing the activated carbon fibers with pulp or a monwoven web and forming the mixture into a shape suitable for the carrier member.

The insect-repellents can alternatively be retained by any of various other methods. For example, a bath can be prepared to contain a liquid in which 5 to 500 g of cockroach-repellent is dissolved per square meter. A carrier member of desired shape is then dipped into the bath to thereby adsorb the dissolved repellent. Alternatively, repellents can be sprayed onto a carrier member. A chamber filled with a repellent in a gaseous condition is prepared and a carrier member is passed through the chamber to adsorb the repellent thereon. When the carrier member is a sheet or film, it can be passed between a pair of coating rolls onto which repellent is supplied, to thereby coat the repellent on the carrier member.

The following table shows some of the results of a test. It is apparent from this and other results that a cockroach-repellent sheet according to the present invention maintain its repellent effect for a long period of time.

PREFERRED EMBODIMENT OF THE INVENTION

One example of the invention uses activated carbon fibers having an average diameter of about 10 $\mu m$, a specific surface area of about 800 $m^2/g$ and fine pores of an average diameter of about 24 A. The activated carbon fibers are mixed into a paper in an amount of 30 $g/m^2$ to produce a paper containing activated carbon fibers having a basis weight of 60 $g/m^2$. The paper is then cut to a predetermined size to make a carrier member. The cockroach-repellent used has a specific gravity of 0.995 to 1.005, a boiling point of 165° to 170° C. under a pressure of 15 mmHg, and a molecular weight of 191. The cockroach-repellent is adsorbed on the carrier member at the rate of 100 g per 1 $m^2$. The resultant cockroach-repellent sheet 3 was subjected to the following test.

Figure 1:
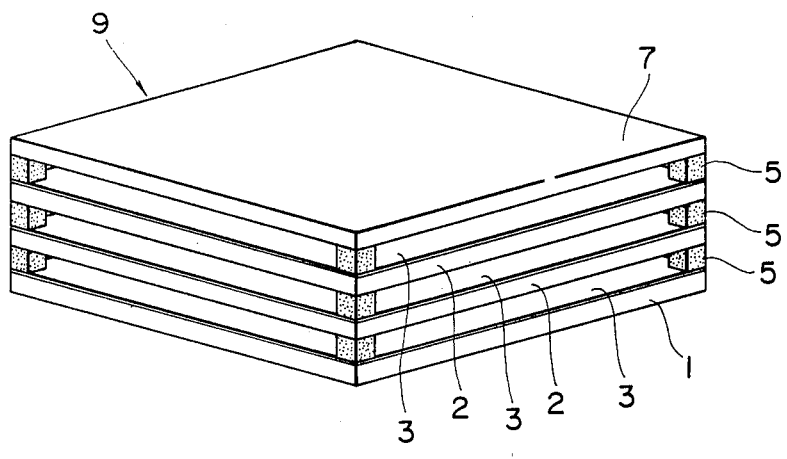
FIG. 1 is a perspective view of a shelter provided with a cockroach-repellent sheet according to the present invention; and, FIG. 2 is a plan view showing the locations in a test room of shelters as shown in FIG. 1 and other shelters having no repellent sheets.
Figure 2:
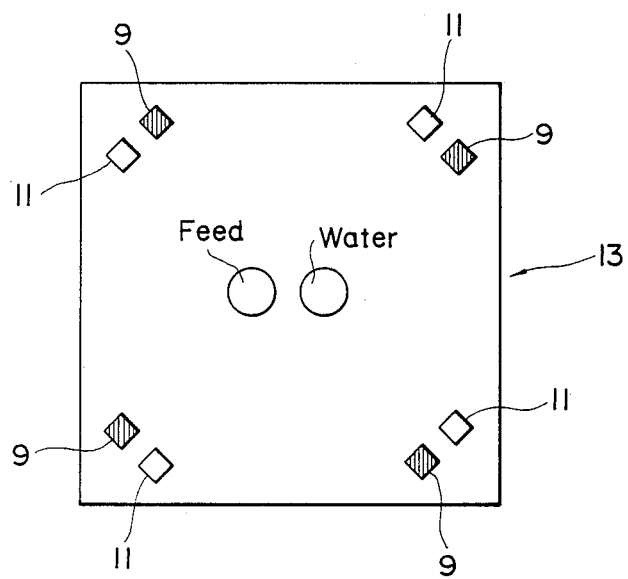

As shown in FIG. 1, a 4 mm × 10 cm × 10 cm veneer board 1 was applied on one surface with the cockroach-repellent sheet 3 using adhesive tapes. Three such boards 1, 1, 1 were stacked as separated from each other by cork spacers 5 in such a way that the sheet 3 of each board faced upwards. Then, a veneer board 7 of the same size but without a sheet 3 was placed on the upper board 1 via coak spacers 5 to produce a shelter 9 having the repellent sheets. On the other hand, a shelter 11 was prepared having the same construction as the shelter 9 except that it was not applied with the repellent sheets 3.

Then, these two kinds of shelters 9, 11 were placed on the floor at each corner of a room 13, as shown in FIG.

2. The room 13 had a floor measuring 120 cm by 120 cm. The height of the room was 15 cm.

50 male and 50 female cockroaches (*Blattella germanica*) were released into the room 13. Thereafter the number of cockroaches hiding in each shelter were counted as once a day. During the test, the shelters were moved clockwise to the next corner after each head count in order to equalize the conditions among the shelters.

TABLE

| Number of cockroaches found in each type of shelter | | | |
|---|---|---|---|
| | TIME | | |
| | 1 day | 2 days | 3 days |
| Shelters 9 | 0 | 0 | 0 |
| Shelters 11 | 146 | 178 | 158 |
| Index of repellency | 100 | 100 | 100 |

Note 1: Number is a sum of those in shelters 9 or shelters 11.
Note 2: Index of repellency = (1-number in shelters 9/number in shelters 11) × 100

We claim:

1. An insect-repellent assembly comprising a carrier member containing activated carbon fibers and an insect-repellent agent contained in said carrier member.

2. The insect-repellent assembly as set forth in claim 1 wherein said carrier member has a felt-like structure and contains activated carbon fibers of about 5 to 50μ in diameter at a basis weight of about 50 to 500 gram per square meter.

3. The insect-repellent assembly as set forth in claim 1 wherein said carrier member has a woven web-like structure and contains activated carbon fibers of about 5 to 50μ in diameter by basis weight of about 50 to 500 gram per square meter.

4. The insect-repellent assembly as set forth in claim 1 wherein said carrier member has a random-web-like structure and contains activated carbon fibers of about 5 to 50μ in diameter at a basis weight of about 50 to 500 gram per square meter.

5. The insect-repellent assembly as set forth in claim 1 wherein said carrier member is composed of a paper at a weight of 10 to 400 gram per square meter containing therein 10 to 95 weight percent of activated carbon fibers.

6. The insect-repellent assembly as set forth in claim 1 wherein said carrier member is composed of a nonwoven web having a basis weight of 10 to 400 gram per square meter and containing therein 10 to 95 weight percent of activated carbon fibers.

7. The insect-repellent assembly as set forth in claim 1 wherein said insect-repellent agent is contained in said carrier member at the rate of 5 to 500 gram per square meter of said carrier member.

8. The insect-repellent assembly as set forth in claim 2 wherein said insect-repellent agent is contained in said carrier member at the rate of 5 to 500 gram per square meter of said carrier member.

9. The insect-repellent assembly as set forth in claim 3 wherein said insect-repellent agent is contained in said carrier member at the rate of 5 to 500 gram per square meter of said carrier member.

10. The insect-repellent assembly as set forth in claim 4 wherein said insect-repellent agent is contained in said carrier member at the rate of 5 to 500 gram per square meter of said carrier member.

11. The insect-repellent assembly as set forth in claim 5 wherein said insect-repellent agent is contained in said carrier member at the rate of 5 to 500 gram per square meter of said carrier member.

12. The insect-repellent assembly as set forth in claim 6 wherein said insect-repellent agent is contained in said carrier member at the rate of 5 to 500 gram per square meter of said carrier member.

13. The insect-repellent assembly as set forth in claim 1 wherein said insect-repellent agent is a cockroach-repellent agent.

14. The insect-repellent assembly as set forth in claim 2 wherein said insect-repellent agent is a cockroach-repellent agent.

15. The insect-repellent assembly as set forth in claim 3 wherein said insect-repellent agent is a cockroach-repellent agent.

16. The insect-repellent assembly as set forth in claim 4 wherein said insect-repellent agent is a cockroach-repellent agent.

17. The insect-repellent assembly as set forth in claim 5 wherein said insect-repellent agent is a cockroach-repellent agent.

18. The insect-repellent assembly as set forth in claim 6 wherein said insect-repellent agent is a cockroach-repellent agent.

19. The insect-repellent assembly as set forth in claim 7 wherein said insect-repellent agent is a cockroach-repellent agent.

20. The insect-repellent assembly as set forth in claim 8 wherein said insect-repellent agent is a cockroach-repellent agent.

21. The insect-repellent assembly as set forth in claim 9 wherein said insect-repellent agent is a cockroach-repellent agent.

22. The insect-repellent assembly as set forth in claim 10 wherein said insect-repellent agent is a cockroach-repellent agent.

23. The insect-repellent assembly as set forth in claim 11 wherein said insect-repellent agent is a cockroach-repellent agent.

24. The insect-repellent assembly as set forth in claim 12 wherein said insect-repellent agent is a cockroach-repellent agent.

* * * * *